United States Patent [19]

Morris et al.

[11] Patent Number: 5,126,261
[45] Date of Patent: Jun. 30, 1992

[54] HIGH CALCIUM CHEMICALLY DEFINED CULTURE MEDIUM

[75] Inventors: Rebecca J. Morris, Austin; Susan M. Fischer, Bastrop; Thomas J. Slaga, Austin, all of Tex.

[73] Assignee: Board of Regents, The University of Texas System, Austin, Tex.

[21] Appl. No.: 337,143

[22] Filed: Apr. 12, 1989

[51] Int. Cl.$^5$ .......................... C12N 5/06; C12N 5/00
[52] U.S. Cl. ........................... 435/240.21; 435/240.31
[58] Field of Search ....................... 435/240.31, 240.21

[56] References Cited

U.S. PATENT DOCUMENTS 4,786,599  11/1988  Chessebeuf et al. ............ 435/240.31

FOREIGN PATENT DOCUMENTS 0076647  4/1983  European Pat. Off.
3711699A1  11/1988  Fed. Rep. of Germany
WO84/03710  9/1984  France

OTHER PUBLICATIONS

McLane, et al., Effect of confluency and extracellular calcium on Proliferation and differentiation of Human Keratinocyte . . . , Clinical Research, vol. 36, No. 3, p. 673A, Apr. 1988.
Morris et al., A New Medium for Primary Cultures of Adult Murine Epidermal Cells: Application to Experimental Carcinogenesis, Cancer Letters, vol. 34, pp. 297-304.
GIBCD Laboratories Catalogue & Reference Guide, pp. 162, 166, 170 1987.
Fuchs et al., Regualted of Terminal Differentiation of Cultured Human Keratinocytes by Vitamin A Cell, vol. 25, pp. 617-625.
Yamane, Development and Application of a Serum--Free Culture Medium for Primary Culture in Nutritional Requirements of Cultured Cells, Kasuta (ed.) Japan Scientific Societies Press (Tokyo) University Park Press (Baltimore) pp. 1-21 1978.
Steven T. Boyce, B. A., et al., Calcium-Regulated Differentiation of Normal Human Epidermal Keratinocytes in Chemically Defined Clonal Culture and Serum-n-Free Serial Culture. The Journal of Investigative Dermatology, 81:33s-40s 1983.
Anne E. Kilkenny et al., Correlation of Initiating Potency of Skin Carcinogens with Potency to Induce Resistance to Terminal Differentiation in Cultured Mouse Keratinocytes. Cancer Research 45,2219-2225, May 1985.
Wallace L. McKeehan, et al., Improved Medium for Clonal Growth of Human Diploid Fiobroblasts At Low Concentrations Of Serum Protein. In Vitro vol. 13, 1977.
Reference AU John F. Lechner et al., Clonal Growth of Normal Adult Human Bronchial Epithelial Cells In A Serum-Free Medium. In Vitro vol. 18, No. 7, Jul. 1982, 0073-5655/82/0633-0642.
Reference AV Hideki Kawamura, et al., Association of Resistance to Terminal Differentiation with initiation of Carcinogenesis in Adult Mouse Epidermal Cells. [Cancer Research 45,2748-2752, Jun. 1985].
Reference AW Henry Hennings, et al., Calcium Regulation of Growth and Differentiation of Mouse Epidermal Cells in Culture. Cell, vol. 19,245-254, Jan. 1980.
Reference AX Henry Hennings, et al., Calcium Regulation of Cell-Cell Contact and Differentiation of Epidermal Cells in Culture. 1983 by Academic Press, Inc. 0014-4827/83/010127-16. Experimental Cell Research, vol. 143, pp. 127-142.
Fischer, et al. Phorbol Ester Induction of 8-Lipoxygenase in Inbred Sencar (SSIN) but not C57BL/6J Mice Correlated with Hyperplasia, Edema, and Oxident Generation but not Ornithine Decarboxylase Induction[1], Cancer Research 48, 658-644, Feb. 1, 1988.
Belury, et al. Eicosapentaenoic and Arachidonic Acid: Comparison of Metabolism and Activity in Murine Epidermal Cells. Lipids, vol. 24, No. 5 (1989) pp. 423-429.
Morris, et al. New Methods for Measuring Cellular Proliferation in the Skin Abstract of presentation, Dec. 1, 1989.
Morris, R. J., et al., A chemically defined, "high" calcium medium for primary cultures of adult murine epidermal cells, abstract for Poster Presentation, Dec. 1, 1989.
Morris, R. J., et al., abstract 816, Proceedings of the American Association for Cancer Research, vol. 30, Mar. 1989, p. 206.
International Search Report for International Application No. PCT/U.S. 90/00471.

Primary Examiner—John Doll
Assistant Examiner—George C. Elliott
Attorney, Agent, or Firm—Arnold, White and Durkee

[57] ABSTRACT

A high calcium chemically defined animal cell culture medium including vitamins A and D and a fatty acid or its ester. The medium is particularly adapted for the primary or secondary culture of epithelial cells. However, the medium may be utilized for establishing and maintaining cell lines, in particular myelomae and hybridomae.

13 Claims, No Drawings

HIGH CALCIUM CHEMICALLY DEFINED CULTURE MEDIUM

BACKGROUND OF THE INVENTION

The United States government may have rights in this patent because of relevant developmental work supported by Research Grant No. CA43278 from National Institutes of Health.

For many years researchers have attempted to perfect a cell culture medium which enabled animal cells to proliferate in vitro. Two general types of cell culture medium have been developed: culture medium supplemented with pituitary extract or serum (Serum-Supplemented Medium: SSM), and chemically defined media without serum (Chemically Defined Medium: CDM). With respect to SSM, the addition of serum to the culture medium introduces a very large number of undefined components. Among these are regulatory compounds, that is to say compounds which regulate cell metabolism. Compounds such as these complicate the study of the regulatory mechanisms which control the proliferation, differentiation and longevity of animal cells. Moreover, in the case of industrial use of established animal cell lines, the presence of serum or of other unknown or poorly defined components creates difficulty in purifying the one or more biological products produced by the cells. In addition, because many biological products cannot be purified, the non-defined composition of SSM leads to prohibitions against human utilization of these biological products by the international and national health authorities (FDA, Ministries of Health, and the like).

One type of SSM which has been used extensively in research is "high" calcium SSM. "High" calcium medium is defined as medium having greater than 0.1 mM calcium. Several researchers have demonstrated the importance of calcium in culture medium. Long term primary cultures of epidermal cells have been difficult to establish and maintain in high calcium medium. "Low" calcium medium is defined as medium having less than 0.1 mM calcium. It has been reported that in "low" calcium medium, although keratinocytes will proliferate, they neither stratify, make desmosomes, nor produce keratins characteristics of their terminal differentiation (1). However, increasing the concentration of calcium in these media induces failure to proliferate, terminal differentiation and sloughing of all normal epidermal cells (2, 3, 4). In the past, a selection with "high" calcium medium has provided an excellent vehicle for assaying for carcinogen or virally altered epidermal cells, as well as the factors involved in the induction of terminal differentiation (2, 5, 6, 7, 8). Nevertheless, "high" calcium SSM is inappropriate for any studies dependent upon concomitant proliferation and differentiation such as, comparing the proliferation potential of normal untreated epidermal subpopulations, or for biological, toxicological, and metabolic studies which may be influenced by undefined components in the medium.

To overcome the various drawbacks presented by cell lines established in "high" calcium SSM, various authors have replaced serum with hormones, electrolytes, and growth factors, such as, insulin, calcium and epidermal growth factor, to create "high" calcium CDM. However, none of these media have been as successful as the "high" calcium SSM in establishing and cultivating primary and secondary cell cultures. The present inventors previously developed a "high" calcium CDM which was used to establish and cultivate epidermal cells from adult mice. This formulation, however, was found to be inferior to a companion "high" calcium SSM with regard to culture longevity (1). Accordingly, a new "high" calcium CDM is needed which overcomes the problems associated with "high" calcium SSM and prior "high" calcium CDM.

A new "high" calcium CDM which is superior or equal to "high" calcium SSM and prior "high" calcium CDM in establishing and cultivating animal cell offers many advantages over prior animal cell culture medium. Among these are: 1) the long term growth and proliferation of freshly isolated animal cells; 2) ease of purifying biological products from the medium for therapeutic applications; and 3) the ability to conduct metabolic, toxicological, and carcinogenesis studies without interference by undefined factors.

The present inventors have developed a chemically defined, "high" calcium animal cell culture medium. The inventive medium now enables researchers to investigate the influence of biological and xenobiotic agents on the outgrowth and subsequent longterm maintenance of normal animal cells obtained from explants or primary cultures of dispersed cells. The defined composition of the present inventive medium and its ability to support the growth and differentiation of animal cells in vitro should be useful for a number of studies related to carcinogenesis, toxicology, cell metabolism and pharmacology, for example in a murine model system, that have not previously been possible.

SUMMARY OF THE INVENTION

The present invention is directed to a high calcium chemically defined animal cell culture medium. The medium includes, in combination, a synthetic basal medium designed for animal cell culture, a retinoid such as vitamin A at a concentration of from about 0.01 to about 1.0 mg/l vitamin $D_2$ at a concentration of from about 0.01 to about 0.5 mg/l and a fatty acid or its ester at a concentration of from 0.01 mg to about 1 mg/l. The medium is particularly adapted for the primary and secondary culture of epithelial cells.

The present invention further involves a method for the primary culture of epithelial cells comprising incubating said cells in a high calcium chemically defined animal cell culture medium. The preparation of such media is also a component of the present invention. In one aspect, the medium of the present invention includes:

(a) a synthetic basal medium designed for animal cell culture;
(b) retinoid such as vitamin A at a concentration of from about 0.01 to about 1.0 mg/l;
(c) vitamin $D_2$ at a concentration of from about 0.01 to about 0.5 mg/l;
(d) a fatty acid or its ester at a concentration of from about 0.01 mg to about 1 mg/l; and
(e) calcium at a concentration of from about 0.1 mM to about 1.4 mM.

Preferred synthetic basal media of the present culture medium include MCDB-151 and SPRD-110. The retinoid such as vitamin A used in this medium is preferably at least one form of retinoid selected from the group consisting of retinyl acetate, retinol, retinal, retinoic acid, retinyl palmitate, retinyl acetate being preferred (particularly at a concentration of about 0.115 mg/l). The vitamin $D_2$ of the medium may be a reduction product of vitamin $D_2$ such as dihydrotachysterol. The fatty acid of the medium is preferably one or more of arachidonic acid, palmitic acid, stearic acid, oleic acid, and linoleic acid. Arachidonic acid and linoleic acid are especially preferred (particularly at a concentration of 0.100 mg/l). The above described medium preferably contains calcium at a concentration of about 1.2 mM.

In a broad aspect the chemically defined cell culture medium of the present invention may be used for any animal cell culture but is particularly preferred for culture of primary or secondary epithelial cells. A preferred medium for these purposes may be partially summarized as a medium including:

(a) a synthetic basal medium designed for animal cell culture;
(b) retinyl acetate at a concentration of from about 0.01 to about 1.0 mg/l;
(c) ergocalciferol at a concentration of from about 0.01 to about 0.5 mg/l;
(d) linoleic acid at a concentration of from 0.01 mg to about 1.0 mg/l; and
(e) calcium at a concentration from about 0.1 mM to about 1.4 mM.

In greater detail, the present invention involves a method for the primary culture of epithelial cells comprising incubating said cells in a high calcium chemically defined cell culture medium, including:

(a) a synthetic basal medium designed for animal cell culture;
(b) an amino acid supplement;
(c) a vitamin supplement;
(d) a mineral supplement, said mineral supplement including from about 0.1 mM to about 1.4 mM calcium;
(e) a trace element supplement;
(f) a growth supplement;
(g) retinyl acetate at a concentration of from about 0.01 to about 1.0 mg/l;
(h) ergocalciferol at a concentration of from about 0.01 to about 0.5 mg/l; and
(i) linoleic acid or its ester at a concentration of from about 0.01 to about 1.0 mg/l.

The medium itself and its preparation also constitute part of the present invention. The preferred amino acid supplement is MEMAAS (see exemplary material for definition) and is usually from about 5 to about 50 ml (most preferably about 20 ml) of the amino acid supplement is added to each 1000 ml of the synthetic basal medium. The preferred vitamin supplement is MEMVS and from about 1 to about 30 ml (preferably about 10 ml) of the vitamin supplement is preferably added to each 1000 ml of the synthetic basal medium. The preferred mineral supplement includes calcium, iron, zinc, magnesium and sodium each of which may be added to the synthetic basal medium separately. Calcium is present in a most preferred concentration of about 1.2 mM. The trace element supplement preferably includes selenium, manganese, silicon, molybdenum, vanadium, nickel and tin. The amino acid supplement, the vitamin supplement, the mineral supplement, the trace element supplement, and the growth supplement are included with the synthetic basal medium. A preferred synthetic basal medium used is SPRD-110. Preferred growth supplements include one or more of delipidized bovine serum albumin, insulin, transferrin, epidermal growth factor, glutamine, phosphoethanolamine, ethanolamine, an antibiotic and a corticosteroid. The antibiotic preferred for use in this medium is a broad spectrum antibiotic such as one or both of penicillin or streptomycin, usually at a concentration of from about 50,000 to about 1,000,000 units/l and from about 50,000 to about 1,000,000 units/l respectively (most preferably they are both present at a concentration of about 100,000 units/l). The most preferred concentration of retinyl acetate is about 0.115 mg/l, and of ergocalciferol—about 0.100 mg/l. The linoleic acid is present at a preferred concentration of about 0.100 mg/l.

In greater detail, a preferred high calcium chemically defined cell culture medium of the present invention is one wherein about 1100 ml of said medium includes:
(a) MCDB media-151 1000ml;
(b) MEM amino acid solution 20 ml;
(c) MEM vitamin solution 10 ml;
(d) About 130 mg of $CaCl_2$;
(e) About 0.4 mg of $FeSO_4.7H_2O$;
(f) About 122 mg of $MgCl_2.6H_2O$;
(g) About 0.86 mg of $ZnSO_4. 7H_2O$;
(h) About 3.50 mg of $Na_2SO_4$;
(i) Trace element supplement 10 ml;
(j) About 1.1 grams of delipidized bovine serum albumin;
(k) About 5 mg of insulin;
(l) About 10.0 mg of transferrin;
(m) About 120 mM glutamine;
(n) About 5.6 mg of phosphoethanolamine;
(o) About 2.4 mg of ethanolamine;
(p) About 100,000 units of penicillin;
(q) About 100,000 units of steptomycin;
(r) About 1 mg of hydrocortisone;
(s) About 10 micrograms of epidermal growth factor
(t) About 0.12 mg of retinyl acetate;
(t) About 0.1 mg of ergocalciferol; and
(u) About 0.1 mg of linoleic Acid.

DESCRIPTION OF THE PREFERRED EMBODIMENTS

The present invention is directed toward a "high" calcium chemically defined cell culture medium for establishing and cultivating animal cells, preferably epithelial cells. This cell culture medium does not contain serum or other undefined supplements and is suitable for both the primary culture of animal cells and for the establishment of cell lines from this primary culture or others. The present inventor has demonstrated that the addition of retinyl acetate, ergocalciferol and linoleic acid to a "high" calcium chemically defined media results in surprising and unexpected cell growth and differentiation. These results were superior to those previously observed in other "high" calcium chemically defined or serum supplemented cell culture medium.

According to one preferred embodiment, a high calcium chemically defined animal cell culture medium is provided which includes: (a) a synthetic basal medium designed for animal cell culture; (b) vitamin A at a concentration of about 0.01 to about 1.0 mg/l; (c) vitamin $D_2$ at a concentration of about 0.01 to about 0.5 mg/l; and (d) a fatty acid or its ester at a concentration of 0.01 to about 1 mg/l.

The synthetic basal medium of the present invention may be one of several commercially available synthetic basal medium customarily used for the culture of animal cells. However, the most preferred synthetic basal medium is MCDB-151 (for example, catalog No. 9061; Irvine Scientific, Santa Ana, Calif.). MCDB-151 has the following composition:

| MCDB MEDIA 151 | |
| --- | --- |
| COMPONENT | MCDB 151 mg/l |
| L-Alanine | 8.91 |
| L-Arginine HCl | 210.7 |
| L-Asparagine.$H_2O$ | 15.01 |
| L-Aspartic Acid | 3.99 |
| L-Cysteine HCl.$H_2O$ | 42.02 |
| L-Glutamic Acid | 14.71 |
| L-Glutamine | 877.2 |
| Glycine | 7.51 |
| L-Histidine HCl.$H_2O$ | 16.77 |
| L-Isoleucine | 1.97 |
| L-Leucine | 65.58 |
| L-Lysine HCl | 18.27 |
| L-Methionine | 4.48 |
| L-Phenylalanine | 4.96 |
| L-Proline | 34.53 |
| L-Serine | 63.06 |
| L-Threonine | 11.91 |
| L-Tryptophan | 3.06 |
| L-Tyrosine. 2Na.$2H_2O$ | 3.92 |
| L-Valine | 35.13 |
| d-Biotin | 0.0146 |
| D-Ca Pantothenate | 0.238 |
| Choline Chloride | 13.96 |
| Folic Acid | 0.794 |
| I-Inositol | 18.02 |
| Niacinamide | 0.0366 |
| Pyridoxine HCl | 0.0617 |
| Riboflavin | 0.0376 |
| Thiamine HCl | 0.0337 |
| Vitamin $B_{12}$ | 0.407 |
| Adenine HCl | 30.89 |
| DL-a-Lipoic Acid | 0.206 |
| Putrescine 2HCl | 0.161 |
| Thymidine | 0.727 |
| $CaCl_2$ (anhyd) | 3.33 |
| KCl | 111.83 |
| $MgCl_2.6H_2O$ | 122.0 |
| NaCl | 7599. |
| $Na_2HPO_4$ (anhyd) | 283.96 |
| $CuSO_4.5H_2O$ | 0.00250 |
| $FeSO_4.7H_2O$ | 0.417 |
| $ZnSO_4.7H_2O$ | 0.863 |
| Glucose | 1081. |
| HEPES | 6600. |
| Phenol Red. sodium salts | 1.242 |
| Sodium Acetate.$3H_2O$ | 500. |
| Sodium Pyruvate | 55.02 |
| $NaHCO_3$ | 1176. |
| | pH 7.4 before $NaHCO_3$ addition use 5% $CO_2$ |

Vitamin A (retinol) is included in the inventive medium in concentrations of 0.01 to about 1.0 mg/l. Most preferably, however, vitamin A is present at a concentration of about 0.115 mg/l.

Vitamin A acid (retinoic acid) is a naturally-occurring metabolite of vitamin A which possesses substantially the same or greater biological activity in epithelial cells compared with the parent compound, vitamin A (retinol). The term "vitamin A", for the purpose of this invention, includes the many other forms of retinol such as retinyl acetate, retinoic acid, retinal and the like. Thus, any of the oxidation states of retinol, variants of retinol, retinoic acid, esters of retinoic acid, variants of retinoic acid or synthetic retinoids with biological activity substantially similar to retinol or retinoic acid may be utilized in the practice of the present invention. For example, the most preferred form of vitamin A is retinyl acetate. According to another preferred embodiment retinyl palmitate is included in the inventive medium. According to still another preferred embodiment retinal, the aldehyde of vitamin A, is present in the inventive medium. In a further preferred embodiment, retinoic acid is present in the inventive medium. Accordingly, vitamin A (retinol), any of its derivative forms, retinoic acid, any of its derivative forms or synthetic retinoids with biological activity substantially similar to retinol or retinoic acid may be utilized in the practice of the present invention.

Vitamin $D_2$ (ergocalciferol), a form of vitamin D derived from vegetable sources, is present in the inventive medium at a concentration of from 0.01 to about 0.5 mg/l. Vitamin $D_3$ (calciferol) is the physiologically equivalent compound derived from animal sources. Most preferably, vitamin $D_2$ is present at a concentration of about 0.10 mg/l. The term "vitamin D", for the purpose of this invention, includes any and all vitamin $D_2$ and vitamin $D_3$ derivatives, including their hydroxylated metabolites, and synthetic or naturally-derived compounds which possess substantial vitamin D-like biological activity. Thus, any of the pharmaceutically acceptable forms of vitamin D may be utilized in the practice of the present invention, for example, dihydrotachysterol (a reduction product of vitamin $D_2$). However, according to the most preferred embodiment, ergocalciferol (vitamin $D_2$) is included in the inventive medium.

A fatty acid is present in the inventive medium at a concentration of from 0.01 mg to about 1.0 mg/l, and most preferably at a concentration of about 0.1 mg/l. The most preferred fatty acid is linoleic acid. It should be noted, however, that other fatty acids or their esters, for example, arachidonic acid, palmitic acid, stearic acid, and oleic acid may be utilized in the practice of the present invention.

The chemically defined medium of the present invention is a "high" calcium medium. A "high" calcium medium is a medium having from about 0.1 mM to about 1.4 mM calcium. The media of the present invention are preferably within this range and most preferably have a calcium concentration of 1.2 mM.

The cells cultivated in the inventive medium are animal cells, and are most preferably epithelial cells. However, cells lines, such as, hybrodomae and myelomae may also be cultivated in the inventive medium.

According to another preferred embodiment, a chemically defined "high" calcium animal cell culture medium is provided which includes: a synthetic basal medium designed for animal cell culture; retinyl acetate at a concentration of from about 0.01 to about 1.0 mg/l; linoleic acid at a concentration of from about 0.01 to about 1.0 mg/l; and ergocalciferol at a concentration of from about 0.1 to about 0.5 mg/l.

According to a further preferred embodiment, a chemically defined cell culture medium is provided including: a synthetic basal medium designed for animal cell culture; an amino acid supplement; a vitamin supplement; a mineral supplement; a trace element supplement; a growth factor supplement; retinyl acetate at a concentration of from 0.01 to about 1.0 mg/l; ergocalciferol at a concentration of from about 0.01 to about 0.5 mg/l; and linoleic acid or its ester at a concentration of from about 0.01 to about 1.0 mg/l.

An amino acid supplement is included in the inventive medium. The most preferred amino acid supplement is Modified Eagles Media Amino Acid Solution 50×(MEMAAS) (for example, CAT 13-606 Whitaker, M.A. Bioproducts). The formulation of MEMAAS is as follows:

| AMINO ACIDS | (mg/l) |
| --- | --- |
| L-Arginine.HCl | 6320.00 |
| L-Cystine | 1200.00 |
| L-Histidine HCl.H₂O | 2100.00 |
| L-Isoleucine | 2620.00 |
| L-Leucine | 2620.00 |
| L-Lysine.HCl | 3650.00 |
| L-Methionine | 750.00 |
| L-Phenylalanine | 1650.00 |
| L-Threonine | 2380.00 |
| L-Tryptophan | 510.00 |
| L-Tyrosine | 1810.00 |
| L-Valine | 2340.00 |

According to one preferred embodiment, from about 5 to about 50 ml of the amino acid supplement is added per liter to the synthetic basal medium, most preferably, MCDB-151. According to the most preferred embodiment about 20 ml MEMAAS is added to every 1000 ml of the synthetic basal cell medium. It should be noted, however, that the amino acid supplement set forth above, MEMAAS, is illustrative of amino acid formulations which may be used in the present invention, and other amino acid supplements may be utilized in the practice of the present invention.

A trace element supplement is included in the inventive medium. The most preferred formulation for the trace element supplement is provided in McKeehan, WL et al., In vitro, 13:399-416 (1977) (9). According to the most preferred embodiment, the trace element supplement of the present invention is prepared according to the following recipe: a 1 liter stock solution is prepared for each of the following trace elements in the following concentrations: 0.3869 g of $H_2SeO_3$/liter $H_2O$; 0.0198g of $MnCl_2.4H_2O$/liter of water; 14.2100 grams of $Na_2SiO_3.9H_2O$/liter of $H_2O$; 0.1236 grams of $(NH_4)_6Mo_7O_{24}.4H_2O$/liter $H_2O$; 0.0585 grams of $NH_4VO_3$/liter $H_2O$; 0.0131 grams of $NiSO_4.6H_2O$/liter of $H_2O$; 0.0113 grams of $SnCl_2.2H_2O$/liter of 0.02N HCl; and then add 1 ml from each liter of the above stock solutions and 0.1 ml of 1N HCl to 92.9 ml of $H_2O$ to make 100 ml of trace element supplement. The final solution should be filtered after the pH of the final solution is adjusted to between 7 and 7.5. From 1 to about 30 ml of trace element supplement is added to every 1000 ml of the synthetic basal medium, most preferably the synthetic basal medium is, MCDB-151. According to the most preferred embodiment, 10 ml of trace element supplement is added to every 1000 ml of synthetic basal medium.

A vitamin supplement is included in the inventive medium. The most preferred vitamin supplement of the present invention is Modified Eagles Media Vitamin Solution (MEMVS) (for example, 100×, CAT. 13-607, Whitaker, M.A. Bioproducts). Following is the formulation for Eagles Modified Media Vitamin Solution:

| VITAMINS | mg/l |
| --- | --- |
| D.Ca.Pantothenate | 100.00 |
| Choline Chloride | 100.00 |
| Folic Acid | 100.00 |
| I-Inositol | 200.00 |
| Nicotinamide | 100.00 |
| Pyridoxal.HCl | 100.00 |
| Riboflavin | 10.00 |
| Thiamine.HCl | 100.00 |

According to one preferred embodiment, from about 1 to about 30 ml of the vitamin supplement is added to about every 1000 ml of the synthetic basal medium. However, most preferably, about 10 ml of the vitamin supplement is added to every 1000 ml of the synthetic basal medium. The vitamin supplement formulation set forth above is illustrative of vitamin supplements which can be utilized in the practice of the present invention.

A mineral supplement is included in the inventive medium. Preferably, the mineral supplement includes calcium, iron, zinc, magnesium and sodium. According to the most preferred embodiment, the above minerals are present as the following salts: $CaCl_2$; $FeSO_4.7H_2O$; $MgCl_2.6H_2O$; $ZnSO_4.7H_2O$; $Na_2SO_4$. $CaCl_2$ is preferably added to the synthetic basal medium in an amount from about 13.0 to about 150 mg 1, and most preferably in an amount of about 130 mg/l. $FeSO_4.7H_2O$ is preferably added to the synthetic basal medium in an amount from about 0.04 to about 1.2 mg/l, and most preferably in an amount of about 0.4 mg/l. $MgCl_2.6H_2O$ is preferably added to the synthetic basal medium in an amount of from about 12.0 to about 244.0 mg/l, and most preferably in an amount of about 122.0 mg 1. $ZnSO_4.7H_2O$ is added to the basal medium in an amount of from about 0.08 to about 1.7 mg, and most preferably in an amount of about 0.86 mg/l. $Na_2SO_4$ is added to the synthetic basal medium in an amount from about 0.35 to about 7.0 mg/l, and most preferably in an amount of about 3.50 mg/l.

Growth supplements are also included in the present invention. According to the most preferred embodiment, the growth supplement includes: delipidized bovine serum albumin (BSA), insulin, transferrin, epidermal growth factor, glutamine, phosphoethanolamine, ethanolamine, a broad spectrum antibiotic, and a corticosteroid. The individual constituents of the growth supplement may be added to the synthetic basal medium separately or together after mixing. Regardless of how they are added, the amount of each growth supplement constituent added to 1000 ml of the synthetic basal medium is, according to one preferred embodiment, as follows: from about 0.50 to about 2.3 grams of delipidized BSA, and most preferably about 1.30 grams of delipidized BSA; from about 1.0 to about 10.0 mg of insulin, and most preferably about 5.0 mg of insulin; from about 2 to about 20.0 mg of transferrin, and most preferably about 10.0 mg transferrin; from about 50 mM to about 200 mM glutamine, and most preferably about 120 mM of glutamine; from about 1.0 to about 11.2 mg of phosphoethanolamine, and most preferably about 5.6 mg phosphoethanolamine; from about 0.24 to about 7.2 mg of ethanolamine, and most preferably about 2.4 mg of ethanolamine; from about 1 to about 30 micrograms of epidermal growth factor, and most preferably about 10 micrograms of epidermal growth factor; from about 50,000 to about 1,000,000 units of penicillin, and most preferably about 100,000 units of penicillin; from about 50,000 to about 1,000,000 of streptomycin, and most preferably about 100,000 units of streptomycin, and from 0.1 to about 5 mg of hydrocortisone, and most preferably about 1.0 mg of hydrocortisone.

The following examples are included to further describe the present invention and are not intended to limit the invention unless otherwise specifically indicated herein.

EXAMPLES

A chemically defined, "high" calcium culture medium was formulated to investigate the outgrowth and subsequent long term maintenance or normal adult murine epidermal cells from explants of dorsal skin. In this investigation, the relative diameters of explants from normal skin were used together with the morphological appearance of the cultures at three weeks to evaluate several medium. Vitamins A and D, as well as linoleic acid were added separately or together to the SPRD-110 medium at concentrations of 0.115 mg/l, 0.100 mg/l. and 0.100 mg/l, respectively. Cutaneous explants of one square millimeter from medium treated with a supplement or control medium (SPRD-110 alone) all demonstrated epidermal outgrowth within one week. Some explants achieved diameters of seven millimeters by three weeks, and thereafter proliferated to confluence with concomitant terminal differentiation.

Preparation of the Explants

Untreated female SSIN mice seven to nine weeks of age were sacrificed by cervical dislocation, dorsal hair clipped, and washed with Prepodine (American Sterilizer Co., Erie, Penna.) and 70% ethanol in water. The dorsal skin was excised and placed in sterile calcium and magnesium free Dulbecco's phosphate-buffered saline. Each skin was removed to a sterile petri dish and every trace of subcutaneous fat and muscle removed by scraping with a scalpel. Pieces of one square mm were cut with a sharp scalpel and placed onto Corning tissue culture dishes previously coated with a collagen-fibronectin mixture according to Lechner, J. et al. In Vitro 18: 633–642, 1982 (10). Approximately ten minutes were allowed for the pieces to adhere to the dish before addition of the culture medium.

Culture Conditions

The explants were cultured in SPRD-110 medium alone. SPRD-110 medium and 0.115 mg/1 retinyl acetate, SPRD-110 medium and 0.100 mg/l linoleic acid, SPRD-110 medium and 0.1 mg/l ergocalciferol, or SPRD-110 medium and 0.115 mg/l retinyl acetate, 0.100 mg/l linoleic acid, and 0.1 mg/l ergocalciferol. Retinyl acetate was obtained from GIBCO, Grand Island, N.Y. Linoleic acid was obtained as linoleic acid conjugated bovine serum albumin from Sigma Chemical Company, St. Louis, Mo. Ergocalciferol was obtained from Sigma Chemical Company, St. Louis, Mo. SPRD-110 medium is a "high" calcium, chemically defined medium previously developed by the present inventor to support long-term primary cultures of adult murine epidermal cells under conditions permissive of both proliferation and terminal differentiation (1). The formula of SPRD-110 may be described as follows: SPRD-110 is a modified MCDB-151 medium supplemented by the addition of (suppliers given as examples):
a) 20 ml/l MEMAAS;
b) 10 ml/l MEMVS;
c) 10 ml/l trace element supplement, prepared according to McKeehan, WL. et al., In Vitro 13: 399–416, 1977;
d) 1.30 grams/l of delipidized bovine serum albumin (Sigma);
e) 5.0 mg/l of insulin (bovine: Sigma I-6634);
f) 10 micrograms/l of epidermal growth factor (collaborative #40001);
g) 5.6 mg/l of phosphoethanolamine (Sigma P-0503);
h) 2.45 mg/l of ethanolamine (Sigma E-9508);
i) 10 mg/l of transferrin (human: Sigma T-1147);
j) 100,000 units/l of penicillin (GiBCO);
k) 100,000 units/l of streptomycin (Whittaker);
l) 1 mg/l of hydrocortisone (Sigma H-0888);
m) 130.81 mg/l of $CaCl_2$;
n) 0.417 mg/l of $FeSO_4.7H_2O$;
o) 122.0 mg/1 of $MgCl_2.6H_2O$;
p) 0.863 mg/l $ZnSO_4.7H_2O$;
q) 3.51 mg/l $Na_2SO_4$; and
r) enough distilled $H_2O$ to make a final volume of 1135 ml.

All cutaneous explants from adult mice were established on dishes coated with Vitrogen-fibronectin (10). This coating had been shown to be important for establishing and maintaining cultures of freshly harvested adult murine epidermal cells (1). The explants were incubated at 36° C. in an atmosphere of 5% $CO_2$ and 95% air. The medium was changed twice weekly beginning three days after the explants were prepared. As appropriate, the cultures were treated at each medium change with SPRD-110 medium alone, with SPRD-110 medium and retinyl acetate (0.115 mg/l; GIBCO, Grand Island, N.Y.), with SPRD-110 medium and linoleic acid conjugated bovine serum albumin (0.100 mg/l linoleic acid; Sigma Chemical Company, St. Louis, Mo.), with SPRD-110 medium and ergocalciferol (0.100 mg/l; Sigma Chemical Company, St. Louis, Mo.), or with SPRD-110 medium and retinyl acetate 0.115 mg/l, linoleic acid 0.001 g/l, and ergocalciferol 0.100 g/l. After three weeks, the cultures were fixed with formalin, stained with Rhodamine B, and the diameters of the explants measured. The diameter of each explant was calculated from measurement in two dimensions. Statistical significance was determined by Student's t Test. Other cultures were prepared for light and electron microscopy (1).

Results

Regardless of the medium, by four days in vitro, epidermal outgrowth had usually begun in many of the explants and was present in most by seven days. Many mitotic figures were present in the radially advancing outgrowth. Although some stratification accompanied the advancing outgrowth, it was greatest in the regions closest to the explant itself. Electron Microscopy of the epithelial outgrowth disclosed many of the typical morphological characteristics of proliferating and differentiating epidermal cells in vivo including: basal cells with mitochondria, ribosomes, microtubules, desmosomes, and numerous keratin bundles throughout the cytoplasm. The proliferative layer was overlayed by a variable number of differentiating cells of which the most superficial demonstrate keratohyalin granules, nuclear degeneration, and cornified envelopes.

The diameters of the explants were recorded at three weeks and the morphology of the cultures was studied using an electron microscope morphological characteristics, such as, shape, size, and adherence were recorded. These results are summarized in Table I.

TABLE I

| Effects of Retinyl Acetate, Calciferol and Linoleic Acid on Adult Murine Epidermal Outgrowth[1] | | | | |
|---|---|---|---|---|
| Supplement | Number of Explants[2] | Diameter[3] (mm) | Morphology[5] | Longevity[6] |
| SPRD-110 medium | 25 | 2.7 ± 0.90 | + | + |
| 0.115 mg/l retinyl acetate (A) | 42 | 4.8 ± 2.0[4] | ++ | + |
| 0.100 mg/l linoleic acid | 19 | 2.7 ± 0.93 | + | ++ |

TABLE I-continued

Effects of Retinyl Acetate, Calciferol and Linoleic Acid on Adult Murine Epidermal Outgrowth[1]

| Supplement | Number of Explants[2] | Diameter[3] (mm) | Morphology[5] | Longevity[6] |
|---|---|---|---|---|
| (LA) 0.1 mg/l ergocalciferol (D2) | 11 | 2.3 ± 0.41 | + - | - |
| SPRD-110 medium + A + LA + D2 | 51 | 4.8 ± 1.6[4] | + + + | + + + |

[1]Cutaneous explants from untreated adult mice were established on dishes coated with Vitrogen fibronectin, cultured for three weeks in supplemented or unsupplemented SPRD-110 medium, fixed in formalin, stained, and measured.
[2]Total number of explants measured in three to four separate experiments
[3]Average ± S.D.
[4]Values are significantly larger than that of SPRD-110 medium alone (p 0.0001 by Student's t test).
[5]Favorable morphological considerations include uniformly compact, polygonal proliferative cells with slightly rounded rather than flat appearance. Differentiated cells are flat and platelike, and generally adherent to the proliferating cells
[6]The relative abundance of mitotic figures in the epithelial outgrowth after two weeks, and eventual proliferation to confluence were considerations used to evaluate longevity.

The addition of the retinyl acetate alone to SPRD-110 medium nearly doubled the explant diameter. Light microscopy confirmed that this increase was due primarily to an increase in the number of proliferative cells rather than to an increase in the relative size of the cells. Although the addition of linoleic acid alone to SPRD-110 medium did not increase the size of the epidermal outgrowths, its addition resulted in an apparent increase in the longevity of the cultures. Longevity was determined by the relative abundance of mitotic figures in the epithelial outgrowth after two weeks, and eventual proliferation to confluence. The addition of ergocalciferol (Vitamin $D_2$) alone to SPRD-110 medium resulted in an improved morphology and uniformity of the epidermal outgrowth rather than in an increased diameter of the explants. The addition of all three of the supplements to the SPRD-110 medium nearly doubled the explant diameter and improved morphology and longevity beyond what was observed in trials using the supplements separately. Moreover, epidermal outgrowth from explants cultured in this formulation grew to confluence by seven to nine weeks, this was not observed in any other medium.

Thus, on the basis of the data set forth above, the present inventor has demonstrated that the addition of retinyl acetate, ergocalciferol, and linoleic acid to a synthetic basal medium, surprisingly and unexpectedly resulted in improved epithelial cell morphology, proliferation, differentiation and longevity.

Changes obvious to those skilled in the art may be made in the various components, steps and procedures described herein without departing from the concept and scope of the invention as defined in the following claims.

The citations in the following list are incorporated by reference herein for the reasons cited.

References

1. Rebecca J. Morris, Kay C. Tacker, James K. Baldwin, Susan M. Fischer and Thomas J. Slaga, "A New Medium For Primary Cultures of Adult Murine Epidermal Cells: Application To Experimental Carcinogenesis", Cancer Letters, 34 (1987) 297-304, Elsevier Scientific Publishers Ireland Ltd.
2. Fischer, S.M. (1985) Use of Marine Keratinocyte Culture In Studying Molecular and Cellular Aspects of Transformation. In: In Vitro Models for Cancer Research Vol. 3, pp. 275-300. Editor: M.M. Webber, CRC Press, Inc. Boca Raton, Fla.
3. Hennings, H. and Holbrook, K. (1983) Calcium Regulation of Cell-Cell Contacts and Differentiation of Epidermal Cells in Culture. Exp. Cell Res., 143, 127-142.
4. Hennings, H., Michael, D., Cheng, C., Steinert, P., Holbrook, K. and Yuspa, S.H. (1980) Calcuim Regulation of Growth and Differentiation in Mouse Epidermal Cells in Culture. Cell, 19, 245-254.
5. Kawamura, H., Strickland, J.E. and Yuspa, S.H. (1985) Association of Resistance to Terminal Differentiation With Initiation Of Carcinogenesis In Adult Mouse Epidermal Cells. Cancer Res., 45, 2748-2757.
6. Kilkenney, A.E., Morgan, D., Spangler, E.F. and Yuspa, S.H. (1985) Correlation of Initiating Potency of Skin Carcinogens With Potency To Induce Resistance to Terminal Differential In Cultured Mouse Keratinocytes, Cancer Res., 45, 2219-2225.
7. Kulesz-Martin, M.F., Koehler, B., Hennings, H. and Yuspa, S.H. (1980) Quantitative Assay For Carcinogen Altered Differentiation In Mouse Epidermal Cells, Carcinogenesis, 1, 955-1006.
8. Yuspa, S.H., Hennings, H., Kulesz-Martin, M.F. and Lichti, U. (1980) The Study of Tumor Promotion In A Cell Culture Model For Mouse Skin: A Tissue That Exhibits Multistage Carcinogenesis In Vitro. In: Carcinogenesis Vol. 7, Mechanisms of Tumor Promotion and Cocarcinogenesis, pp. 171-188. Editors: E. Hecker, N.E. Fusenig, W. Kunz, F. Marks and H.W. Thielmann. Raven Press, New York.
9. McKeehan, Wl., McKeehan, K.A., Hammond, S.L., and Ham, R.g. Improved medium for clonal growth of human diploid fibroblasts at low concentrations, In Vitro, 13:399-416, (1977).
10. Lechner, J.F., Haugen, A.A., McClendon, I.H. and Pettis, E.W. (1982) Clonal Growth of Normal Adult Human Bronchial Epithelial Cells in a Serum-Free Medium. In Vitro, 18, 633-642.

What is claimed is:

1. A method for the primary culture of epidermal cells to confluence characterized by proliferating cells and terminally differentiated cells, the method comprising incubating epidermal cells in a high calcium chemically defined animal cell culture medium which includes:
   (a) SPRD-110 synthetic basal medium;
   (b) retinoid at a concentration of from about 0.01 to about 1.0 mg/l;
   (c) vitamin D at a concentration of from about 0.01 to about 0.5 mg/l;
   (d) linoleic acid or its ester at a concentration of from about 0.01 mg/l to about 1 mg/l; and
   (e) calcium at a concentration of from about 0.1 mM to about 1.4 mM.

2. The method of claim 1 wherein the retinoid is one or more of retinyl acetate, retinol, retinal, retinoic acid, and retinyl palmitate.

3. The method of claim 1 wherein the retinoid is retinyl acetate.

4. The method of claim 1 wherein the vitamin D is a reduction product of vitamin $D_2$, dihydrotachystrol.

5. The method of claim 3 wherein the retinyl acetate is present at a concentration of about 0.115 mg/l.

6. The method of claim 1 wherein the vitamin D is vitamin $D_2$, and is present at a concentration of 0.100 mg/l.

7. The method of claim 1 wherein the linoleic acid is present at a concentration of about 0.100 mg/l.

8. The method of claim 1 wherein the calcium is present at a concentration of about 1.2 mM.

9. A method for the primary culture of epidermal cells to a point of confluence characterized by proliferating cells and terminally differentiated cells, the method comprising incubating epidermal cells in a chemically defined animal cell culture medium, the medium including:

(a) SPRD-110 synthetic basal medium;
(b) retinyl acetate at a concentration of from about 0.01 to about 1.0 mg/l;
(c) ergocalciferol at a concentration of from about 0.01 to about 0.4 mg/l;
(d) linoleic acid at a concentration of from 0.01 mg to about 1.0 mg/l; and
(e) calcium at a concentration from about 0.1 mM to about 1.4 mM.

10. The method of claim 9 wherein the retinyl acetate is present at a concentration of about 0.115 mg/l.

11. The method of claim 9 wherein the ergocalciferol is present at a concentration of about 0.100 mg/l.

12. The method of claim 9 wherein the linoleic acid is present at a concentration of about 0.100 mg/l.

13. The method of claim 9 wherein the calcium is present at a concentration of about 1.2 mM.

* * * * *

UNITED STATES PATENT AND TRADEMARK OFFICE
CERTIFICATE OF CORRECTION

PATENT NO.    :   5,126,261
DATED         :   June 30, 1991
INVENTOR(S)   :   Rebecca J. Morris, Susan M. Fischer, Thomas J. Slaga It is certified that error appears in the above-identified patent and that said Letters Patent is hereby corrected as shown below:

```
In claim 4, column 12, line 63, delete the term
     "dihydrotachystrol" and insert the term
     --dihydrotachysterol-- therefor.
```

Signed and Sealed this

Fourteenth Day of December, 1993

Attest:

BRUCE LEHMAN

Attesting Officer          Commissioner of Patents and Trademarks